(12) United States Patent
Bischoff et al.

(10) Patent No.: US 11,617,789 B2
(45) Date of Patent: Apr. 4, 2023

(54) PROCESS FOR THE PREPARATION OF ALLERGENIC EXTRACTS

(71) Applicant: Jubilant HollisterStier LLC, Spokane, WA (US)

(72) Inventors: Donald A. Bischoff, Spokane, WA (US); Shannon E. Brown, Spokane, WA (US); Matthew M. Wright, Spokane, WA (US); Derek W. Constable, Spokane, WA (US)

(73) Assignee: Jubilant HollisterStier LLC, Spokane, WA (US)

( * ) Notice: Subject to any disclaimer, the term of this patent is extended or adjusted under 35 U.S.C. 154(b) by 710 days.

(21) Appl. No.: 16/678,432

(22) Filed: Nov. 8, 2019

(65) Prior Publication Data

US 2020/0147208 A1 May 14, 2020

Related U.S. Application Data

(60) Provisional application No. 62/758,189, filed on Nov. 9, 2018.

(51) Int. Cl.
*A61K 39/35* (2006.01)
*A61K 35/646* (2015.01)
*A61K 35/36* (2015.01)

(52) U.S. Cl.
CPC .............. *A61K 39/35* (2013.01); *A61K 35/36* (2013.01); *A61K 35/646* (2013.01)

(58) Field of Classification Search
None
See application file for complete search history.

(56) References Cited

U.S. PATENT DOCUMENTS

| 2,316,311 | A | 4/1943 | Boatner |
| 3,148,121 | A | 9/1964 | Strauss |
| 3,148,122 | A | 9/1964 | Strauss |
| 3,591,677 | A | 7/1971 | Kramer |
| 3,953,588 | A | 4/1976 | Nieschulz et al. |
| 4,234,569 | A | 11/1980 | Marsh |
| 5,770,698 | A | 6/1998 | Berrens |
| 7,887,821 | B2 | 2/2011 | Jacobi et al. |
| 2007/0237877 | A1* | 10/2007 | Diosady ............ A23L 2/52 426/598 |
| 2011/0177582 | A1* | 7/2011 | Trass ............ A23K 10/37 435/272 |
| 2012/0148626 | A1* | 6/2012 | Moingeon ............ A61P 37/02 424/275.1 |
| 2013/0195888 | A1 | 8/2013 | Wang |

FOREIGN PATENT DOCUMENTS

JP 3302418 B2 7/2002

OTHER PUBLICATIONS

Noon L., "Prophylactic Inoculation Against Hayfever," Lancet 1911:1572-3 (1911).

* cited by examiner

*Primary Examiner* — Nora M Rooney
(74) *Attorney, Agent, or Firm* — William D. Hare, Esq.; McNeely, Hare & War, LLP

(57) ABSTRACT

Disclosed herein are methods for the preparation of allergenic extracts. In one embodiment, the methods are carried out without having to adjust the pH of the extraction phase. The methods provide efficient recovery of allergenic extract from allergenic source material.

30 Claims, No Drawings

PROCESS FOR THE PREPARATION OF ALLERGENIC EXTRACTS

This application claims the benefit of U.S. Provisional Patent Application Ser. No. 62/758,189, filed Nov. 9, 2018, which is hereby incorporated by reference in its entirety.

FIELD

Disclosed herein are processes for the preparation of an allergenic extract, which involve efficient recovery of allergenic extract from allergenic source material. The allergenic extracts obtained are stable, and upon reconstitution have substantially reduced amounts of, or are devoid of, any precipitation due to aggregation, chemical reaction, salt formation, etc., compared to allergenic extracts prepared from other processes.

BACKGROUND

Allergy is an acquired hypersensitivity disorder of the immune system, and is triggered by exposure to harmless environmental substances known as allergens. The allergic reaction is mediated by the formation of IgE class antibodies directed against the allergens of concern. Binding of allergen with these antibodies initiates a cascade of inflammatory responses that manifests the symptoms of allergy that can include asthma, rhinitis, allergic eczema, conjunctivitis, and allergic shock. These responses can be initiated by allergens present in animal dander (e.g., cat, dog, horse); pollens, such as ragweed; micro fungi, such as *alternaria*; insects, such as mite and cockroach; and foods, such as peanuts and milk.

In 1911 a pollen allergen extract was first used for the treatment of pollen allergic rhinitis (Noon, "Prophylactic Inoculation Against Hayfever," Lancet 4:1572 (1911)). Since then, allergenic extracts have played an important role in diagnosis and treatment of allergic diseases. These extracts are administered subcutaneously, orally, or as skin patches.

The preparation of allergenic intermediates involving efficient recovery of allergenic extracts from allergenic source materials typically revolves around 3 factors: (i) source material characteristics, (ii) processing of the material to obtain an allergen extract (or allergenic intermediate), and (iii) extract storage. The source material characterization depends upon the source from which the allergen is to be extracted. Processing involves extraction of allergen from source material and bringing the allergenic intermediate into a state to be useful for diagnosis or treatment. Once prepared, the correct storage conditions play a role in keeping the extract stable and sterile to meet regulatory standards for distribution and use.

Of all the aspects involved in obtaining an allergenic intermediate, a significant challenge lies at the processing stage. The first step in processing involves contacting a source material, i.e., the solid allergenic biological raw material such as, e.g., pollen, house dust mites, animal epithelia, insects, or molds, with a liquid extracting solution. Once contacted with a liquid extracting solution to form a mixture of source material and extracting solution, the mixture is stirred, milled, or sonicated to release allergenic protein from the solid source material. The allergenic protein is then subjected to separation, to separate solid from liquids. Since the amount of allergenic protein is proportionally small compared to the bulk of source solid material from which it is extracted, a very efficient process is required to extract and recover the desired material and minimize loss in waste. At the same time, the process needs to be convenient as well as time and energy efficient. A typical process of filtration for separation of solids from liquids employs centrifugation and dead end filtration, individually or in sequence, to carry out separation, clarification, and filtration. Dead end filtration involves use of membranes of progressively smaller pore size to yield a particulate free solution. Such a process has limitations as it involves loss of products at each stage of separation and clarification whenever a smaller pore size filtration step takes place to remove particulates from solution. Thus, to get a desired solution, the process is bound to carry out multiple clarifications and with each step there is loss of yield, which multiplies the loss in terms of time, energy, and process capability to produce desired results. Another operational disadvantage associated with a typical process is blockage of dead end filters which is due to high solid to liquid ratio and again leads to loss of yield and operational difficulties.

Allergenic extracts are water soluble biological components, often comprised of a complex mixture of proteins, carbohydrates, enzymes, dyes, etc. One of the major risks involved with use of allergenic extracts is that their administration to a sensitized patient can cause severe allergic reactions or anaphylaxis. Thus, preparation and maintenance of a safe and effective allergenic extract using a robust method is important to ensure its purity, potency, safety, stability, and sterility during preparation, handling, storage, and distribution.

Active allergenic extracts typically include protein allergens having a molecular weight of about 10-100 kDa, whereas molecules with a molecular weight lower than 10 kDa may bring out additional toxic or irritant side effects in patients. Accordingly, efficient removal of low molecular weight molecules is a desirable objective for allergenic extract preparation.

Allergenic extracts are often produced as highly concentrated biological solutions. The main factor that limits how concentrated an allergen immunotherapy extract can be is the tendency of highly concentrated antigen solutions to develop precipitates. This is an unpredictable and poorly understood phenomenon. Although there is no evidence that such precipitates adversely affect allergenic extracts, the U.S. Food and Drug Administration, through implementation of the U.S. Pharmacopeia general chapter <1> Injections, does not permit a manufacturer to ship an extract that has a precipitate.

Precipitation arises due to aggregation of soluble components to form insoluble particulates, reactions, or by a combination of components to form insoluble salts, rendering an allergenic extract unsuitable for immunotherapy and other purposes despite having been prepared by a lengthy and tedious process. Consequently, special emphasis must be directed to the manufacturing process to obtain yields more consistent in lot-to-lot composition and having the requisite stability to meet regulatory requirements and customer expectations.

U.S. Pat. No. 2,316,311 discloses a process for the preparation of allergenic extracts. According to this process, raw materials are extracted into an aqueous extracting fluid and then purified or concentrated by subjecting the extract to fractional precipitation by the addition of a suitable ether, ketone, or mono-hydroxy alcohol. The most preferred solvent used was acetone and subsequent treatment with a salt, such as ammonium sulfate, sodium sulfate, or zinc sulfate. This process suffers from inefficient removal of low molecular weight molecules, and so it is no longer used.

U.S. Pat. Nos. 3,148,121 and 3,148,122 disclose a process for preparing allergenic extracts, which involves treating whole allergenic substances with an aqueous heterocyclic amine extracting fluid, separating the liquid phase containing the active principals, and discarding the residue. To separate the active substances from the heterocyclic amine, water and an alum solution are added in order to precipitate the allergenic components. Since the most commonly used heterocyclic amine was pyridine, the process is commonly called the pyridine extracted alum precipitated ("PEAP") process. Over the years, several limitations appeared with allergenic extracts prepared by the PEAP process. For example, pyridine used during the extraction alters the natural structure of the extract, rendering it largely inactive and not suitable for skin testing purposes. Further, the process is cumbersome with yields in the range of about 50% based on the Protein Nitrogen Unit (PNU) content of the original extract. Thus, this process is not suitable for preparing allergenic extracts on a commercial scale.

U.S. Pat. No. 3,591,677 discloses a process for preparing an extract useful for hyposensitization therapy involving precipitating the active principles using an aluminium compound such as potassium aluminium sulfate. This process initially involves the treatment of aqueous extracted fluid with a heterocyclic tertiary amine, such as pyridine, picoline, lutidine, etc. Since the process also involves use of heterocyclic amines, which need high temperature treatment for their removal from extracted allergenic substances, denaturing of allergens can occur. Therefore, this process has limitations. Further, the extracts obtained from this process are not suitable for diagnostic purposes.

U.S. Pat. No. 3,953,588 discloses a process involving pre-extraction, where the allergen-containing material is treated with a lipophilic solvent, which is a cyclic ether selected from the group of tetrahydrofuran, tetrahydropyran, and dioxane before aqueous extraction of allergen material. This pre-treatment not only removes any lipophilic portion present in allergen-containing material, but also takes along with it some portion of allergen contacting material. Thus, this process involves not only the use of ethers having mutagenic effects, but also leads to yield loss. Accordingly, this process has limitations based on safety concerns and low yield.

U.S. Pat. No. 4,234,569 discloses a method for production of allergen extracts, which involves the treatment of allergen extract with formaldehyde or lower saturated aliphatic aldehyde which modifies the allergen. Thus, this process does not provide allergens in their natural form, but rather they are provided in modified form, which is not effective for diagnosis and may reduce efficacy in immunotherapy.

U.S. Pat. No. 5,770,698 discloses a method for the preparation of allergenic extract, which involves preparing an aqueous extract containing allergenically active proteins to which undesirable non-allergenic compounds (e.g., low molecular weight compounds) are adhered. This process involves disrupting electrostatic, hydrophobic, or other physical forces. Under such conditions, the non-allergenic compounds disadhere from allergenically active proteins. The disruption is brought about by treatment with an acid having a pH value of less than 3, or by electric currents in the form of electrophoresis. Thus, the process adds operations, which makes the extraction process lengthier, and acid treatment and electric treatment may alter the allergen extract structure making it less effective. Thus, this process is not ideally suited for allergen extract preparation.

JP Patent No. 3,302,418 discloses a process for the preparation of *Dermatophagoides farinae* mite allergen extract. This process involves treating the mite bodies with saturated sodium chloride, allowing the treated mite bodies to stand, and then subjecting the resulting solid-liquid mixture to centrifugation. Mite bodies are then separated by filtration and the filtrate is subjected to ultrafiltration to remove low molecular weight components. However, this process suffers from an inefficient recovery of extract from mite bodies. Specifically, floating mite bodies have to be removed by filtration, which also filters out allergen components, leading to a loss of yield of the allergen extract. Consequently, this process is not viable for large scale applications.

U.S. Pat. No. 7,887,821 discloses a process for the preparation of an allergenic extract, specifically a pollen allergen, by extraction, dead end filtration, first concentration, diafiltration, conductivity test, second concentration, dry weight adjustment, and clarification by filtration prior to storage. The disclosed process during extraction involves mixing a source material with an extraction buffer in a ratio of 1:10, agitation at 8° C. for 2 hours, and adjusting the pH during extraction from 5 to 9. After extraction, further steps are performed, including diafiltration until a desired conductivity test result is obtained. The process aims to remove low molecular weight components that are potentially toxic from allergen extracts, but is tedious in terms of pH adjustment and carrying out conductivity tests as an end point for diafiltration, which adds steps and requires careful monitoring of the process. This increases the time cycle and cost of the process, making it less than suitable for commercial scale.

U. S. Patent Application Publication No. 2013/195888 discloses the utilization of widely used ultrafiltration and diafiltration processes for extraction of antibody and antigen binding protein products. The resultant extract is further treated with buffer or surfactant to avoid aggregation or precipitation in final preparation. Thus, the disclosed process has a shortcoming in terms of requiring the addition of buffers and/or surfactant additives to make the product stable, and which may alter the composition if applied to allergenic extracts.

Accordingly, it is understood that known allergen extraction processes suffer many disadvantages. These include the inefficient removal of low molecular weight components, such as in acetone precipitation; the use of heterocyclic amines like pyridine for precipitation, which may alter the allergens; employing sophisticated techniques like electrophoresis, which add to cost or require the performance of unnecessary pH adjustments/conductivity tests; or utilizing methods that reduce efficiency of the allergenic extraction process through lower yields, including the use of additives to stabilize the finished product. Thus, keeping in view the utility of allergenic extracts in diagnosis and treatment of allergies, there is an urgent need for the development of a simple and convenient process for the preparation of stable allergenic extracts involving efficient recovery of allergenic extract from allergenic source material to address the shortcomings of the current state of the art.

The present invention is directed to overcoming these and other deficiencies in the art.

SUMMARY

An object of this disclosure is to provide allergen extraction processes that alleviate one or more of the shortcomings of prior disclosed processes.

It is yet another object to provide simplified and efficient processes for the preparation of an allergenic extract.

It is yet a further object to provide simplified, efficient, and convenient processes for the preparation of an allergenic extract, where the allergenic extract obtained substantially reduces or eliminates the potential of precipitation during storage.

It is yet another object to provide processes for the preparation of an allergen extract that do not require the presence of additives to create a stable allergen extract having substantially reduced levels of precipitates, or which is devoid of preciptates.

It is yet another object to provide efficient processes for the recovery of allergen extracts from allergen source materials using cross flow microfiltration.

It is yet another object to provide efficient processes for the recovery of allergen extract from allergen source material using cross flow microfiltration providing down to 0.2 µm clarified crude liquid extract.

One aspect relates to a process for the preparation of an allergenic intermediate. This process involves contacting an allergenic source material with an extraction fluid; extracting biological material from the allergenic source into the extraction fluid; separating the biological material into a solid phase portion and a liquid phase portion to obtain a crude extract; concentrating the crude extract using ultrafiltration to extract and to partially remove low molecular weight molecules (e.g., of less than 5 kDa); subjecting the concentrated extract to continuous diafiltration to remove remaining lower molecular weight molecules from the concentrated extract; and lyophilizing the ultrafiltered and diafiltered extract to obtain the allergenic intermediate. The process is carried out without having to adjust the pH of the extraction fluid during extraction or without a requirement for conductivity testing to determine the endpoint of ultrafiltraion.

Another aspect relates to a process for preparing an allergenic intermediate. This process involves contacting an allergenic source material with an extraction fluid; extracting biological material from the allergenic source into the extraction fluid; recovering a crude extract from the extraction fluid in liquid phase by separating a solid phase from a liquid phase by cross flow microfiltration to remove particulates greater than 0.2 µm-0.8 µm in size; flushing the solid phase with additional solution; concentrating the crude extract using ultrafiltration to further extract and to partially remove low molecular weight molecules (e.g., of less than 5 kDa); subjecting the concentrated extract to continuous diafiltration to remove remaining lower molecular weight molecules in the concentrated extract; and lyophilizing the diafiltered extract to obtain the allergenic intermediate, where the process is carried out without having to adjust the pH of the extraction fluid.

It is known that any chemical treatment is bound to bring about changes to the natural form of any molecule, including the active allergen molecules in allergenic extracts. Thus, the inventors in their quest to find a simple, convenient, and efficient process for the preparation of allergen extracts found that the preparation of highly concentrated allergenic extracts is possible without the need for pH adjustment during the extraction phase of the source material with extraction fluid and when the crude extract obtained is subjected to ultrafiltration and diafiltration. This reduces or eliminates the downstream precipitation issue without the addition of any surfactant and/or additional salts or buffers.

The processes described herein overcome deficiencies in the art by providing a simplified and efficient process for the preparation of stable, non- or substantially non-precipitating allergenic extracts. In addition, the disclosure provides a process involving efficient recovery of allergenic extract from allergenic source material.

DETAILED DESCRIPTION

Disclosed herein are processes for the preparation of an allergenic extract in a simple, convenient way. These processes involve efficient recovery of allergenic extracts from allergenic source material. The allergenic extracts obtained are stable and upon reconstitution are substantially reduced, or devoid of any precipitation due to, e.g., aggregation, chemical reaction, salt formation, and combinations thereof.

One aspect relates to a process for the preparation of an allergenic intermediate. This process involves contacting an allergenic source material with an extraction fluid; extracting biological material from the allergenic source into the extraction fluid; separating the biological material into a solid phase portion and a liquid phase portion to obtain a crude extract; concentrating the crude extract using ultrafiltration to extract and to partially remove low molecular weight molecules (e.g., of less than 5 kDa); subjecting the concentrated extract to continuous diafiltration to remove remaining lower molecular weight molecules from the concentrated extract; and lyophilizing the ultrafiltered and diafiltered extract to obtain the allergenic intermediate. The process is carried out without adjusting the pH of the extraction fluid during said extracting or without requiring conductivity testing to determine the endpoint of ultrafiltration.

The allergenic extract, also referred to as an allergenic intermediate, is an extract of a biological allergen source material containing any naturally occurring protein allergen that induces allergic, i.e., IgE mediated, reactions upon repeated exposure to an individual. Examples of naturally occurring allergens include pollen allergens (tree-, herb, weed-, and grass pollen allergens), insect allergens (inhalant, saliva and venom allergens, e.g., mite allergens, cockroach and midges allergens, hymenopthera venom allergens), animal hair and dandruff allergens (from e.g., dog, cat, horse, rat, mouse etc.), and food allergens. Important pollen allergens from trees, grasses, and herbs are such originating from the taxonomic orders of Fagales, Oleales, Pinales and platanaceae including, among others, birch (*Betula*), alder (*Alnus*), hazel (*Corylus*), hornbeam (*Carpinus*) and olive (*Olea*), cedar (*Cryptomeria* and *Juniperus*), Plane tree (*Platanus*), the order of Poales including, among others, grasses of the genera *Lolium, Phleum, Poa, Cynodon, Dactylis, Holcus, Phalaris, Secale*, and Sorghum, the orders of Asterales and Urticales including, among others, herbs of the genera *Ambrosia, Artemisia*, and *Parietaria*. Other important inhalation allergens are those from house dust mites of the genus *Dermatophagoides* and *Euroglyphus*, storage mite (e.g., Lepidoglyphys, Glycyphagus, and Tyrophagus), those from cockroaches, midges, and fleas (e.g., Blatella, Periplaneta, Chironomus and Ctenocepphalides), and those from mammals such as cat, dog and horse, venom allergens including such originating from stinging or biting insects such as those from the taxonomic order of Hymenoptera including bees (superfamily Apidae), wasps (superfamily Vespidea), and ants (superfamily Formicoidae). Important inhalation allergens from fungi and molds are, among others, those originating from the genera *Alternaria* and *Cladosporium*.

Several allergens are known and may be extracted in the processes described herein. Such allergens may include, for example and without limitation, Bet v 1, Aln g 1, Cora 1, Car b 1, Que a 1, Cry j 1, Cry j 2, Cup a 1, Cups 1, Jun a 1, Jun a 2, Jun a 3, Ole e 1, Lig v 1, Pla l 1, Pla a 2, Amb a 1, Amb a 2, Amb t 5, Art v 1, Art v 2 Par j 1, Par j 2, Par j 3, Sal k 1, Ave e 1, Cyn d 1, Cyn d 7, Dac g 1, Fes p 1, Hol l 1, Lol p 1 and 5, Pha a 1, Pas n 1, Phl p 1, Phl p 5, Phl p 6, Poa p 1, Poa p 5, Sec c 1, Sec c 5, Sor h 1, Der f 1, Der f 2, Der p 1, Der p 2, Der p 7, Der m 1, Eur m 2, Gly d 1, Lep d 2, Blot 1, Tyr p 2, Bla g 1, Bla g 2, Per a 1, Fel d 1, Can f 1, Can f 2, Bos d 2, Equ c 1, Equ c 2, Equ c 3, Mus m 1, Rat n 1, Apis m 1, Api m 2, Ves v 1, Ves v 2, Ves v 5, Dol m 1, Dil m 2, Dol m 5, Pol a 1, Pol a 2, Pol a 5, Sol i 1, Sol i 2, Sol i 3 and Sol i 4, Alt a 1, Cla h 1, Asp f 1, Bos d 4, Mal d 1, Gly m 1, Gly m 2, Gly m 3, Ara h 1, Ara h 2, Ara h 3, Ara h 4, and Ara h 5. Other allergens also exist and will be discovered, and may be extracted using the processes described herein.

In one embodiment, the allergenic intermediates obtained via the processes described herein include, without limtation, Can f 1 and Fel d 1 from epithelial extracts, Der p 1 and Der f 1 from house dust mite extracts, Phl p 5 and Phl p 1 from grass pollen extracts, or Alt a 1 and Asp f 1 from mold extracts.

In one embodiment of the invention the allergen is selected from the group consisting of a tree pollen allergen, a grass pollen allergen, a house dust mite allergen, a storage mite allergen, a weed allergen, a mold allergen, a cat allergen, and a dog allergen.

According to one embodiment, the extraction fluid used in the processes of the present invention may be, for example and without limitation, an aqueous solution of glycerol, sodium chloride, and sodium bicarbonate; or an aqueous solution of sodium chloride, sodium bicarbonate, and a phenolic compound. In one embodiment, the phenolic compound is selected from a phenol, catechol, and the like. Other extraction fluids may also be used.

Suitable extraction fluids include those capable of contacting an allergenic source material, typically in solid form, and extracting biological material from the allergenic source into the extraction fluid. Such extraction creates a mixture containing a solid phase and a liquid phase portion, which is referred to as a crude extract.

In one embodiment, the extraction fluid is mixed with an allergenic source material in a ratio of about 1:4 to about 1:20, or a ratio of about 1:5 to about 1:21. In one embodiment, the allergenic source is contacted with the extraction fluid at a concentration ratio of about 1:4, 1:5, 1:6, 1:7, 1:8, 1:9, 1:10, 1:11, 1:12, 1:13, 1:14, 1:15, 1:16, 1:17, 1:18, 1:19, 1:20, or 1:21. In one particular embodiment, the allergenic source material comprises a house dust mite allergen and the concentration ratio is about 1:14, 1:15, or 1:16, or decimal variations thereof. In another particular embodiment, the allergenic source material comprises animal hair and/or dander allergen and the concentration ratio is about 1:6.1, 1:6.2, 1:6.3, 1:6.4, 1:6.5, 1:6.6, 1:6.7, 1:6.8, 1:6.9, or 1:7.

In the methods described herein, the extraction process may be carried out for about 2 hours and up to about 6 days at a temperature of about 5° C. to 30° C. In one particular embodiment, the allergenic source material comprises a house dust mite allergen and the extraction process is carried out for about 1-6 hours, or about 1 hour, 1.5 hours, 2 hours, 2.5 hours, 3 hours, 3.5 hours, 4 hours, 4.5 hours, 5 hours, 5.5 hours, or 6 hours, at a temperature of about 20° C.-25° C., or about 20° C., 21° C., 22° C., 23° C., 24° C., or 25° C. In another particular embodiment, the allergenic source material comprises animal hair and/or dander allergen and the extraction process is carried out for about 3-5 days, or about 3 days, 3.5 days, 4 days, 4.5 days, or 5 days, at a temperature of about 0° C.-5° C., or 0° C., 1° C., 2° C., 3° C., 4° C., or 5° C.

In one embodiment, depending on the allergenic source material, extraction is carried out by milling the allergenic source material after said contact with the extraction fluid. Thus, according to one embodiment, extracting biological material from the allergenic source into the extraction fluid is carried out under conditions of continuous circulation through a mill or batch wise milling. According to such an embodiment, the allergenic source material may be selected from, e.g., a house dust mite allergen, food allergen, or insect allergen.

According to one embodiment, the extracted source material is liquid phase separated from the solid source material residue, particularly large particles, to recover a crude extract. Such separation may be carried out using techniques well known in the art including, without limitation, dead end filtration, centrifugation, and the like, typically at ambient temperature, although other conditions may also be used.

According to one embodiment, the crude extract is subjected to ultrafiltration to concentrate allergens in the liquid phase, and to remove the majority of low molecular weight molecules having a molecular weight of less than 1 kDa, 2 kDa, 3 kDa, 4 kDa, 5 kDa, 6 kDa, 7 kDa, 8 kDa, 9 kDa, or 10 kDa, to obtain a concentrated extract which contains allergen molecules having a typical molecular weight of between about 10-100 kDa or higher, and some residual low molecular weight molecules. Ultrafiltration refers to any technique in which a solution or a suspension is subjected to a semi-permeable membrane that retains macromolecules while allowing solvent and small solute molecules to pass through. Ultrafiltration may be used to increase the concentration of macromolecules in a solution or suspension.

According to one embodiment, the concentrated extract is further subjected to a process for removal of residual low molecular weight molecules by diafiltration. Diafiltration is a specialized class of filtration in which the retentate is diluted with solvent and re-filtered, to reduce the concentration of soluble permeate components. Diafiltration may or may not lead to an increase in the concentration of retained components, including, proteins. For example, in continuous diafiltration, a solvent is continuously added to the retentate at the same rate as the filtrate is generated. In this case, the retentate volume and the concentration of retained components does not change during the process. On the other hand, in discontinuous or sequential dilution diafiltration, an ultrafiltration step is followed by the addition of solvent to the retentate side; if the volume of solvent added to the retentate side is not equal or greater to the volume of filtrate generated, then the retained components will have a high concentration. Diafiltration may be used to alter the pH, ionic strength, salt composition, buffer composition, or other properties of a solution or suspension of macromolecules.

In one embodiment, diafiltration is carried out in a continuous mode using a buffer solution. In one particular embodiment, the buffer solution used in diafiltration is an aqueous ammonium bicarbonate solution. In one embodiment, the diafiltration process is carried out using about 5 to about 21 diavolumes of buffer solution, or 5, 6, 7, 8, 9, 10, 11, 12, 13, 14, 15, 16, 17, 18, 19, 20, or 21 diavolumes of buffer solution. In one particular embodiment, the allergenic source material comprises animal hair and dander allergen, such as from dog, and diafiltration is carried out according to the proceeses described herein by subjecting concentrated extract to continuous diafiltration using 7, or about 7, or 6-8, or 5-9 diavolumes of buffer solution. In a particular embodiment, the allergenic source material comprises house dust mite allergen and diafiltration is carried out according to the proceeses described herein by subjecting concentrated extract to continuous diafiltration using 10-14 diavolumes of buffer solution, or 11-13 diavolumes of buffer solution, or 10, 11, 12, 13, or 14 diavolumes of buffer solution. According to one embodiment, the resulting diafiltered extract is essentially free from low molecular weight molecules present in the original extract and having a molecular weight of less than 1 kDa, 2 kDa, 3 kDa, 4 kDa, 5 kDa, 6 kDa, 7 kDa, 8 kDa, 9 kDa, or 10 kDa.

According to one embodiment, the ultrafiltered and diafiltered extract is then lyophilized to produce a bulk intermediate which is then processed further to obtain an allergen extract, or an allergenic intermediate. In one embodiment, the diafiltered extract is lyophilized in a lyophilization tray and is then processed further to obtain lyophilized allergen extract.

In one embodiment, the processes described herein are carried out without adjusting pH of the extraction fluid during said extracting. In other words, a stable preparation of an allergenic intermediate may be obtained pursuant to the methods described herein without having to monitor or adjust pH of the extraction fluid while extracting biological material from the allergenic source into the extraction fluid, as is required by other methods of preparing allergenic intermediates.

In another embodiment, the processes described herein are carried out without having to perform conductivity testing to determine a suitable endpoint of ultrafiltration.

In another embodiment, the processes described herein are carried out without adjusting pH of the extraction fluid during said extracting and without having to perform conductivity testing to determine a suitable endpoint of ultrafiltration.

Another aspect relates to a process for preparing an allergenic intermediate. This process involves contacting an allergenic source material with an extraction fluid; extracting biological material from the allergenic source into the extraction fluid; recovering a crude extract from the extraction fluid in liquid phase by separating a solid phase from a liquid phase by cross flow microfiltration to remove particulates greater than 0.2 µm-0.8 µm in size; flushing the solid phase with additional solution; concentrating the crude extract using ultrafiltration to further extract and to partially remove low molecular weight molecules (e.g., of less than 5 kDa); subjecting the concentrated extract to continuous diafiltration to remove remaining lower molecular weight molecules in the concentrated extract; and lyophilizing the diafiltered extract to obtain the allergenic intermediate. The process is carried out without adjusting pH of the extraction fluid.

According to one embodiment, the processes of this aspect of the disclosure involve an efficient process for extraction of allergens from a biological source material, where the process involves cross flow microfiltration for recovery of allergen extract from source material, and where the process alleviates the drawbacks of other known processes. Cross flow microfiltration has advantages over dead end filtration as the dynamic motion of liquid solid phase over the membrane surface prevents the buildup of compacted solid on the surface that reduces the filtration capacity. The use of cross flow microfiltration for allergen extracts combines all stages of separation, clarification, and filtration in a single continuous step which is highly beneficial in terms of yield and operational ease. The process further allows the use of different pore sizes to be employed down to 0.2 µm filtered extract obtained in a single step operation which overcomes the need to use progressively smaller size pore filters required with dead end filtration, which reduces the time consumption and cycle time. The use of cross flow filtration further allows highly improved recovery of soluble allergenic components of the liquid/solid mix, because as the liquid is removed through the filter pores, a wash solution is added to the remaining solid to recover any allergen held up in the solid waste matrix.

In one embodiment, the method further provides a solution to filter blockage commonly encountered with traditional filtration practices by inclusion of back pulsing steps during cross flow microfiltration, which enhances the efficiency of the process many-fold. This process successfully provides a cross flow microfiltration process for efficient extraction of allergen proteins in a liquid phase called crude extract from a solid-liquid mixture. The crude extract obtained is further subjected to ultrafiltration and diafiltration to concentrate high molecular weight allergen components and simultaneously remove low molecular weight components, which are majorly responsible for precipitation effect in a final extract.

In one embodiment, crude extract in liquid phase is separated from solid source material residue, particularly large particles, which constitute undesired components and particulates. Such a separation is carried out by cross flow microfiltration to separate liquid from solid particles to carry out separation, clarification, and filtration in a single process. The cross flow microfiltration may be carried out by using hollow fiber membranes or ceramic filters of 0.2 µm size or 0.8 µm size, or any size in between. The solid material to be discarded may be additionally flushed with buffer solution to recover any trapped extract. In one particular embodiment, the buffer solution used is ammonium bicarbonate. Such a cross flow microfiltration provides 0.2 µm to 0.8 µm clarified crude liquid extract in a single step at ambient temperature.

In one embodiment, the process of cross flow microfiltration is accompanied by back pulsing of filtrate or diluent which removes blockage, if any, in the filters used and avoids loss of allergen extract trapped in blocked solid residue thereby increasing the yield and making the process operationally feasible.

In one embodiment, the diafiltered extract is lyophilized in a lyophilization tray and is then processed further to obtain lyophilized allergen extract.

According to an embodiment, the lyophilized allergenic extracts obtained according to the processes described herein may be further used for reconstitution in various diluents at predetermined concentrations for one or more uses such as in skin prick testing, immunotherapy vaccines, incorporation into solid dose forms for oral treatment, solid phase adsorption to membranes, etc., and including for use in in vitro diagnostic devices.

According to one embodiment, the lyophilized allergen intermediate obtained according to the processes described herein having high molecular weight allergens when reconstituted in solution is substantially reduced or devoid of aggregation, precipitation, or salt formation and is stable within the regulatory guidelines provided for allergenic preparations to be used for diagnostic and treatment therapies.

The processes described herein provide a means of concentrating a protein (i.e., an allergenic agent) to very high levels in solution without the need for additional stabilizing agents. The concentration of the protein in the aqueous formulation obtained using the methods described herein can be any amount in accordance with the desired concentration. Allergen extracts derived from mites are often characterized by units of measure referred to as "AU" for "allergy units," usually as "AU/mL." For other allergens such as from cat and pollen, the term "BAU" is used for "bioequivalent units." For yet other allergens such as from dog, the terminology is w/v, such as 1:20 w/v, which stands for 1 g source material per 20 mL of fluid. The relationship between BAU and 1:20 w/v depends upon the extract. In any event, there is a defined amount of extract contained within the concentrate. In one embodiment, allergenic extracts obtained by the processes described herein may be obtained at potency levels of at least about 10,000 AU/mL; 20,000 AU/mL; 30,000 AU/mL; 40,000 AU/mL; 50,000 AU/mL; 60,000 AU/mL; 70,000 AU/mL; 80,000 AU/mL; 90,000 AU/mL, or any level between 10,000 AU/mL to 90,000 AU/mL. In one particular embodiment, allergenic extracts obtained by the processes described herein are obtained at a potency level of at least 30,000 AU/mL. In one embodiment, allergenic extracts obtained by the processes described herein may be obtained at potency levels of at least about 10,000 BAU/mL; 20,000 BAU/mL; 30,000 BAU/mL; 40,000 BAU/mL; 50,000 BAU/mL; 60,000 BAU/mL; 70,000 BAU/mL; 80,000 BAU/mL; 90,000 BAU/mL, or any level between 10,000 BAU/mL to 90,000 BAU/mL. In one particular embodiment, allergenic extracts obtained by the processes described herein are obtained at a potency level of at least 30,000 BAU/mL. In one embodiment, allergenic extracts obtained by the processes described herein are obtained at conventional yields, such as 1:10 w/v. However, application of the processes described herein allow significantly more concentrated allergenic extracts to be obtained, including concentrations that are a 10-100 fold increase (or any number or range therein) in concentration over conventional yields, such as 1:10 w/v.

According to one embodiment of the processes described herein, the allergenic intermediate is reconstituted after lyophilization. For example, lyophilized material may be combined with reconstitution fluid at a ratio to target a particular concentration of allergenic extract (e.g., 30,000 AU/mL). A suitable reconstitution fluid may include, for example and without limitation, a glycerol-cocas fluid (0.5% sodium chloride, 0.275% sodium bicarbonate, and 52.5% glycerin, in water for injection).

The reconstituted allergenic extract may be clarified. In one embodiment, clarification conditions may include, for example, room temperature (20° C.-25° C.) using a 0.2 μm membrane filter with an in-process bioburden load of less than 1 CFU/mL and storage at 1° C.-5° C. pending sterile filtration.

Sterile filtered extract may then be stored, e.g., in bulk containers at a suitable temperature (e.g., 1° C.-5° C.).

The processes described herein provide the advantage that the resulting preparations of allergenic extract have reduced precipitation potential compared to allergenic extracts prepared by other processes. According to one embodiment, allergenic extracts prepared by the inventive processes are devoid, or substantially devoid, of protein aggregates, despite the high concentration of the aqueous protein. Protein aggregation is a common problem in protein solutions, and often results from increased concentration of the protein. The processes described herein provide a means for achieving a high concentration, low or no protein aggregation allergenic extract. In one embodiment, allergenic extracts achieved from the processes of the described herein do not rely on a buffering system and excipients, including surfactants, to keep proteins in the formulation soluble and from aggregating. Thus, allergenic extracts obtained from the processes described herein are advantageous for therapeutic purposes, as they are high in protein concentration and are water-based, not relying on additional agents to achieve high, stable concentrations of proteins in solution.

Allergenic extracts obtained by the processes described herein may be formulated for administration to a subject or patient. Thus, the allergenic extracts may be used to form pharmaceutical compositions for administration to, e.g., humans.

EXAMPLES

The following examples are provided to illustrate embodiments of the disclosure but they are by no means intended to limit its scope.

Example 1: Preparation of Dog Hair-Dander Allergen

Extraction of Dog Hair-Dander

Dog hair-dander source material was combined with extraction fluid (0.1% sodium chloride, 0.2% sodium bicarbonate, 0.5% liquefied phenol, in water for injection) at a ratio of 1 g:6.4 mL. Nine containers, each containing 10,000 g of dog hair-dander source material and 64,000 mL of extraction fluid, were prepared. The extraction of dog hair-dander source material continued for 3-4 days at 1° C.-5° C.

Initial Clarification of Dog Hair-Dander Extract

To remove gross solids, the extraction mixture was centrifuged. The liquid portion was collected and the solids discarded. The recovered extract was then further clarified using depth filter, followed by membrane filter. The clarified liquid was collected into a holding tank.

Concentration of Dog Hair-Dander Extract

The clarified liquid was concentrated using tangential flow filtration (ultrafiltration) until the concentrated volume was 1.6% of the starting extract (by weight).

Diafiltration of Concentrated Dog Hair-Dander Extract

The resulting extract from above was subjected to diafiltration (buffer exchange) with a 50 mM ammonium bicarbonate exchange buffer to remove the low molecular weight proteins, small molecules, and salts, using seven diavolumes of exchange buffer.

Lyophilization of Concentrated Dog Hair-Dander Extract

Concentrated dog hair-dander extract was distributed into lyophilizer trays and was freeze dried. Upon completion of the lyophilization cycle, the trays were removed and the lyophilized raw material from each tray was pooled together in a storage vessel. Thirty-three grams of lyophilized intermediate raw material were recovered. The lyophilized intermediate raw material was stored at 1° C.-5° C. for long term storage. The raw material had a moisture content of 6.1% and microbial load of less than 10 colony forming units (CFU) per gram of material.

Reconstitution of Lyophilized Dog Hair-Dander Intermediate

Dog hair-dander lyophilized raw material intermediate was combined with reconstitution fluid (0.5% sodium chloride, 0.275% sodium bicarbonate, and 52.5% glycerin, in water for injection) at a ratio of 1 g:650 mL. A thirty liter batch size was manufactured. The mixture was continuously mixed at room temperature to bring the raw material into solution.

Clarification of Glycerinated Dog Hair-Dander Extract

The glycerinated dog hair-dander extract was clarified at room temperature (20° C.-25° C.) using a 0.2 μm membrane filter with an in-process bioburden load of less than 1 CFU/mL and was stored at 1° C.-5° C. pending sterile filtration. The extract was then sterile filtered at room temperature (20° C.-25° C.) using 0.1 μm membrane filters and stored in bulk containers at 1° C.-5° C. pending the filling of final container vials. The final sterile filtered extract had a glycerin content of 53% glycerin, and a total protein concentration of 12,500 Protein Nitrogen Units (PNU) per mL of extract.

Example 2: Preparation of House Dust Mite (HDM) Allergen

Milling and Extraction of Mite Raw Material

Mite source material (*Dermatophagoides farinae*) was combined with Glycero-cocas extraction fluid (0.5% sodium chloride, 0.275% sodium bicarbonate, and 52.5% glycerin, in water for injection) at a ratio of 1 g:15 mL for ten minutes. The starting batch size was 30,000 mL.

A continuous throughput bead mill was used to break open the mite cuticles to release and extract the allergens. The volume of mite mixture was passed through the milling chamber 8.3 times to ensure complete disruption of mite bodies taking 2.5 hours.

Initial Clarification of Mite Extract

To remove gross solids, the extraction mixture was centrifuged at 15° C.-30° C. The liquid portion was collected and the solids were disposed of. The recovered extract was then further clarified at room temperature (20° C.-25° C.) using depth filters, and finally a using a 0.2 μm membrane filter. The clarified liquid was collected into a holding tank.

Concentration of Mite Extract

The resulting clarified extract was concentrated using tangential flow filtration (ultrafiltration) until the concentration target of 10% of the starting extract (by weight) was achieved.

Diafiltration of Concentrated Mite Extract

The resulting extract from above was subjected to diafiltration (buffer exchange) with a 50 mM ammonium bicarbonate exchange buffer to remove the low molecular weight proteins, small molecules, and salts, using fourteen diavolumes of exchange buffer.

Lyophilization of Concentrated Mite Extract

Concentrated mite extract was distributed into lyophilizer trays and was freeze dried. Upon completion of the lyophilization cycle, the trays were removed and the lyophilized raw material from each tray was pooled together in a storage vessel. Thirty-six grams of lyophilized intermediate raw material was manufactured. The lyophilized intermediate raw material was stored at 1° C.-5° C. for long term storage. The potency of the raw material was determined using a potency assay where a 5 milligram/mL preparation had a potency of 30,000 AU/mL.

Reconstitution of Lyophilized Mite Intermediate

Mite lyophilized raw material intermediate was combined with Glycero-cocas fluid (0.5% sodium chloride, 0.275% sodium bicarbonate, and 52.5% glycerin, in water for injection) at a ratio to target a 30,000 AU/mL extract. The formulation was calculated based on the potency of the raw material batch. The batch size was 3,000 mL. The mixture was continuously mixed for 134 minutes at room temperature (20° C.-25° C.) to bring the raw material into solution.

Clarification of Glycerinated Mite Extract

The glycerinated mite extract was clarified at room temperature using a 0.2 μm membrane filter. The extract was stored at 1° C.-5° C. pending sterile filtration. The sterile filtered extract was stored in bulk containers at 1° C.-5° C. pending the filling of final container vials. The potency of the extract was determined to be 30,000 AU/mL.

Example 3: Preparation of House Dust Mite Allergen Using Cross Flow Microfiltration Milling and Extraction of Mite Raw Material Mite source material (*Dermatophagoides farinae*) was combined with Glycero-cocas extraction fluid (0.5% sodium chloride, 0.275% sodium bicarbonate, and 52.5% glycerin, in water for injection) at a ratio of 1 g:15 mL for nine minutes. The batch size was 15,000 mL.

A continuous throughput bead mill was used to break open the mite cuticles to release and extract the allergens. The volume of mite mixture was passed through the milling chamber 10 times to ensure complete disruption of mite bodies taking 1.5 hours.

Initial Clarification of Mite Extract Using Cross Flow Microfiltration

A portion of the crude extract was clarified using cross flow microfiltration having a filter assembly with a 0.8 μm cut-off. The solution was diluted with 50 mM ammonium bicarbonate solution when the feedstock becomes sufficiently concentrated to continue microfiltration and recover additional clarified filtrate. The clarified extract (filtrate) was collected for further processing and concentrated solids (i.e., mite cuticle fragments, particulates) were collected as retentate and disposed of.

Concentration of Mite Extract

The resulting clarified extract was concentrated using tangential flow filtration (ultrafiltration) until a volume 12% of the starting extract (by weight) was achieved.

Diafiltration of Concentrated Mite Extract

The resulting extract from above was subjected to diafiltration (buffer exchange) with a 50 mM ammonium bicarbonate exchange buffer to remove the low molecular weight proteins, small molecules, and salts, using fourteen diavolumes of exchange buffer.

Lyophilization of Concentrated Mite Extract

Concentrated mite extract was distributed into lyophilizer trays and was freeze dried. Upon completion of the lyophilization cycle, the trays were removed and the lyophilized raw material from each tray was pooled together in a storage vessel. The lyophilized intermediate raw material was stored at 1° C.-5° C. for long term storage. The potency of the raw material was determined using a potency assay. A 5 mg/mL preparation of lyophilized raw material had a potency of 30,000 AU/mL.

Reconstitution of Lyophilized Mite Intermediate

Mite lyophilized raw material intermediate was combined with Glycero-cocas fluid (0.5% sodium chloride, 0.275% sodium bicarbonate, and 52.5% glycerin, in water for injection) at a ratio to target a 30,000 AU/mL extract. The formulation was calculated based on the potency of the raw material batch. The mixture was continuously mixed at room temperature (20° C.-25° C.) to bring the raw material into solution. A 5 mg/mL preparation had a potency of 30,000 AU/mL.

Clarification of Glycerinated Mite Extract

The glycerinated mite extract was clarified at room temperature using a 0.2 μm membrane filter. The extract was stored at 1° C.-5° C. pending sterile filtration. The sterile filtered extract was stored in bulk containers at 1° C.-5° C. pending the filling of final container vials.

What is claimed:

1. A process for the preparation of an allergenic intermediate, said process comprising:

contacting an allergenic source material with an extraction fluid, wherein the allergenic source material is contacted with the extraction fluid at a concentration ratio of about 1:15;

milling the allergenic source material after the source material is contacted with the extraction fluid;

extracting a biological material from the allergenic source material into the extraction fluid;

separating the biological material into a solid phase portion and a liquid phase portion to obtain a crude extract;

concentrating the crude extract using ultrafiltration to extract and to partially remove low molecular weight molecules of less than 5 kDa;

subjecting the concentrated extract to continuous diafiltration to remove remaining lower molecular weight molecules from the concentrated extract; and lyophilizing the ultrafiltered and diafiltered extract to obtain the allergenic intermediate, wherein said process is carried out without adjusting pH of the extraction fluid during said extracting or without requiring conductivity testing to determine the endpoint of ultrafiltration.

2. The process according to claim 1 further comprising:
reconstituting the allergenic intermediate and storing the reconstituted allergenic intermediate,
wherein during said storing the reconstituted allergenic intermediate has reduced precipitation potential compared to reconstituted allergenic intermediates prepared by other processes.

3. The process according to claim 1, wherein the allergenic source material is selected from house dust mite allergen, insect allergen, venom allergen, animal hair and dander allergen, food allergen, and combinations thereof.

4. The process according to claim 3, wherein said allergenic source material comprises house dust mite allergen.

5. The process according to claim 1, wherein said extracting is carried out under conditions of continuous circulation through a mill.

6. The process according to claim 5, wherein said extracting is carried out for 1-6 hours.

7. The process according to claim 5, wherein said extracting is carried out at 20° C.-25° C.

8. The process according to claim 7, wherein said subjecting the concentrated extract to continuous diafiltration is carried out using 10-14 diavolumes of buffer solution.

9. The process according to claim 3, wherein said allergenic source material comprises animal hair and dander allergen.

10. The process according to claim 9, wherein said allergenic source is contacted with said extraction fluid at a concentration ratio of about 1:6-7.

11. The process according to claim 9, wherein said extracting is carried out for about 3-5 days.

12. The process according to claim 9, wherein said extracting is carried out at 0° C.-5° C.

13. The process according to claim 9, wherein said subjecting the concentrated extract to continuous diafiltration is carried out using 7 diavolumes of buffer solution.

14. The process according to claim 1, wherein said separating is carried out using centrifugation.

15. The process according to claim 1, wherein said separating is carried out using centrifugation and dead end filtration.

16. The process according to claim 1, wherein said concentrating is carried out in the absence of a conductivity test.

17. The process according to claim 1, wherein said subjecting the concentrated extract to continuous diafiltration is carried out using an aqueous ammonium bicarbonate solution.

18. A process for preparing an allergenic intermediate, said process comprising:
contacting an allergenic source material with an extraction fluid;

extracting biological material from the allergenic source into the extraction fluid;

recovering a crude extract from the extraction fluid in liquid phase by separating a solid phase from a liquid phase by cross flow microfiltration to remove particulates greater than 0.2 μm —0.8 μm in size;

flushing the solid phase with additional solution;

concentrating the crude extract using ultrafiltration to further extract and to partially remove low molecular weight molecules of less than 5 kDa;

subjecting the concentrated extract to continuous diafiltration to remove remaining lower molecular weight molecules in the concentrated extract; and lyophilizing the diafiltered extract to obtain the allergenic intermediate, wherein said process is carried out without adjusting pH of the extraction fluid.

19. The process according to claim 18, wherein said recovering by cross flow microfiltration provides separation, clarification, and filtration in a single process.

20. The process according to claim 19, wherein the cross flow microfiltration provides 0.2 μm—0.8 μm clarified crude liquid extract in a single step.

21. The process according to claim 18, wherein the allergenic source material is selected from house dust mite allergen, insect allergen, venom allergen, animal hair and dander allergen, food allergen, and combinations thereof.

22. The process according to claim 21, wherein said allergenic source material comprises house dust mite allergen.

23. The process according to claim 22, wherein said allergenic source material is contacted with said extraction fluid at a concentration ratio of about 1:15.

24. The process according to claim 23 further comprising:
milling the allergenic source material after said contacting.

25. The process according to claim 24, wherein said extracting is carried out under conditions of continuous circulation through a mill.

26. The process according to claim 25, wherein said extracting is carried out for 1-6 hours.

27. The process according to claim 25, wherein said extracting is carried out at 20-25° C.

28. The process according to claim 23, wherein said subjecting the concentrated extract to continuous diafiltration is carried out using 10-14 diavolumes of buffer solution.

29. The process according to claim 18 further comprising:
reconstituting the allergenic intermediate and storing the reconstituted allergenic intermediate,
wherein during said storing the reconstituted allergenic intermediate has reduced precipitation potential compared to reconstituted allergenic intermediates prepared by other processes.

30. The process according to claim 18, wherein said subjecting the concentrated extract to continuous diafiltration is carried out using an aqueous ammonium bicarbonate solution.

* * * * *